United States Patent [19]

Conner, Jr.

[11] Patent Number: 5,637,810
[45] Date of Patent: Jun. 10, 1997

[54] APPARATUS AND METHOD FOR EFFICIENT DETERMINATION OF EQUILIBRIUM ADSORPTION ISOTHERMS AT LOW PRESSURES

[76] Inventor: William C. Conner, Jr., P.O. Box 175, Montague, Mass. 01351

[21] Appl. No.: 546,942

[22] Filed: Oct. 23, 1995

[51] Int. Cl.⁶ ................................................. G01N 15/08
[52] U.S. Cl. ............................................... 73/865.5; 73/38
[58] Field of Search ...................................... 73/38, 865.5

[56] References Cited

U.S. PATENT DOCUMENTS

| | | | |
|---|---|---|---|
| 3,211,007 | 10/1965 | Atkins | 73/865.5 |
| 3,850,040 | 11/1974 | Orr, Jr. et al. | 73/865.5 |
| 4,566,326 | 1/1986 | Lowell | 73/865.5 |
| 4,762,010 | 8/1988 | Borghard et al. | 73/38 |
| 4,972,730 | 11/1990 | Camp et al. | 73/865.5 |
| 5,058,442 | 10/1991 | Yamanaka et al. | 73/865.5 |
| 5,109,716 | 5/1992 | Ito et al. | 73/38 |

*Primary Examiner*—Robert Raevis

[57] ABSTRACT

This invention provides an apparatus and method whereby variable amounts of adsorbent are dosed over a porous sample to measure the equilibrium amount adsorbed by a sample over more than two orders of magnitude in pressure. The apparatus fills a fixed volume to variable pressures of adsorbent and/or provides multiple doses of adsorbent from a fixed volume in order to change the amount of gas to which the sample is exposed. Thus, a sample is exposed to doses of adsorbent that span over an order of magnitude in amount.

The improved apparatus employs substantially larger capacity tubing and valves (diameters greater than 0.25 inch ID) than those that have been employed in prior apparatuses for the measurement of adsorption by porous solids. Further, the improved apparatus employs a vacuum system capable of substantially lower pressures than those conventionally employed for the measurement of adsorption by porous solids. These innovations allow for a sample to be evacuated efficiently to lower pressures than in prior apparatuses employed for the measurement of equilibrium adsorption by porous solids.

The amount adsorbed is measured after sufficient time is allowed for equilibrium to be achieved (as determined by the changes in adsorbent pressure with time). This time between equilibrium measurements varies throughout a series of measurements.

The disclosed adsorption apparatus and method allow for variations in the amount of adsorbent exposed to the sample for variable periods of time. This enables more efficient measurement of adsorption on porous solids over more than two orders of magnitude in pressure.

31 Claims, 2 Drawing Sheets

APPARATUS AND METHOD FOR EFFICIENT DETERMINATION OF EQUILIBRIUM ADSORPTION ISOTHERMS AT LOW PRESSURES

TECHNICAL FIELD

The present invention relates to techniques for measurement of the equilibrium sorption (adsorption or desorption) isotherms (volume adsorbed versus pressure at a near constant temperature) for porous solids. Volumetric sorption isotherms are primary data by which the surface area, pore volume and pore size distribution are estimated by calculations based on the volume adsorbed versus the relative pressure (P/Po, where Po is the saturation pressure of the sorbate at the temperature of measurement) of an adsorbing gas. The improved apparatus enables the user accurately and efficiently to measure the sorption isotherms over several orders of relative pressure. The apparatus and methods disclosed have a particular advantage over known systems and methods for measurements of adsorption isotherms for microporous solids (i.e., those with minimum dimension less than 2 nm) and/or where the pore volumes are filled at relative pressures below $10^{-3}$.

BACKGROUND ART

The adsorption of gases onto porous solids is a primary method by which the morphology of solids is characterized. Specifically, the surface area, pore volume and pore size distribution can be inferred and calculated from analyses of the relationship between the volume adsorbed and the pressure of a physically adsorbing gas. These morphological characteristics (surface area, pore volume and pore size distribution) are employed in the design and analyses of solids employed in catalysis, as adsorbents or for separations.

A variety of theories are employed to interpret the adsorption or desorption isotherms in order to infer the total surface area of the solid and the dimensions of any void space within or between individual particles. The specific theory and equations employed in the analyses depends on the range of dimensions of pores being analyzed, on the specific adsorbent/adsorbate being analyzed, and on the preference of the person performing the analyses. Nitrogen sorption at 77 K. or Argon sorption at 87 K. (or 77 K.) are often employed in the analyses, although the improved techniques and system are not limited to the use of these adsorbates at these temperatures.

Crucial to each theory and its application to the analyses of the data to infer the morphology of porous solids is the assumption that the data being analyzed represent equilibrium sorption isotherms. The present invention provides a novel apparatus and method to obtain equilibrium adsorption isotherms. Specifically, the system measures multiple data points of the equilibrium sorption isotherms at low pressures (e.g., significantly less than a relative pressure of 0.1, i.e., 0.1 atmospheres for measurement of adsorption at the boiling point of the sorbate) in a reduced period of time.

Several systems and approaches have been patented and are available to measure sorption isotherms. Most of these have involved measurement of sorption for pressures within two orders of magnitude of the saturation pressure (i.e., at relative pressures from 0.01 to 1.0). U.S. Pat. No. 3,850,040 discloses an apparatus and a method by which the amount of gas admitted to the sample system is determined by calculation and manipulation of the pressure of the sorbing gas added to or removed from above a sample maintained at the temperature at which the sorption is to be measured. Examples demonstrate how the amount adsorbed over equal increments of relative pressure (e.g., changes in relative pressure of 0.04) from 0.04 to 0.2 may be measured initially to calculate the surface area of the sample by the BET theory. Subsequently, pore volume analysis is accomplished by "extending the previously-described dosing sequence" along a predetermined series of partial pressures which culminate at a desired pressure, such as 0.99 Po. A diffusion pump (backed up by a roughing pump) is employed to evacuate the sample and a single diaphragm pressure transducer is employed to measure the pressure at which sorption equilibrium is achieved. A method is also described by which desorption is measured from a relative pressure of approximately 0.99 in similarly predetermined increments.
Comments on U.S. Pat. No. 3,850,040

The method and equipment described in this patent are incapable of measuring pressures over more than two decades of relative pressure. The pumping system is inadequate for high resolution adsorption isotherms since minimum tubing and valve sizes are not specified, and a single stage diffusion pump cannot achieve low enough initial pressures. Further, multiple transducers are required to measure pressures accurately over the broad spectrum of pressures (greater than a factor of 10000) required for high resolution adsorption isotherms. Further, there is no provision to vary the increments of adsorbate volume introduced by the amount required for high resolution adsorption (greater than a factor of 100) and there is no provision for changing and monitoring the achievement of equilibrium in volume adsorbed between doses. This is crucial to assuring equilibrium measurements in a reasonable time, particularly commencing at pressures substantially below 0.001 atmospheres ($P/P_o<<0.001$ for a gas at its boiling point) and covering greater than three orders of magnitude in pressure. The current invention discloses all of these novel approaches in equipment and methods of measuring isotherms.

U.S. Pat. No. 4,566,326 discloses an automated apparatus by which the sorption isotherms can be measured independently for a plurality of samples. Several pressure transducers (one per sample) are employed to independently monitor the pressure over several samples essentially simultaneously. A method is described by which gas is admitted from a manifold (at a separately controlled and measured pressure) to each of several samples. This patent describes a system which makes the measurement of sorption isotherms more efficient by conducting the measurements in parallel. The described measurements commence with the calculation of the surface area by adsorption measurements over relative pressures (e.g., from approximately 0.05 to 0.2) through the adsorption and desorption within the pores (nearly up to a relative pressure of 1.0).
Comments on U.S. Pat. No. 4,566,326

This Patent discloses the use of multiple pressure transducers. However, the transducers all span the same range and are each connected to different samples. This invention discloses a single apparatus and methods by which it can be operated to measure adsorption isotherms for several samples in parallel up to less than a factor of 100 in relative pressure. There is no provision to measure a broader range of pressures. There are no disclosures which allow for the equilibrium measurements to start at low relative pressures ($P/P_o<0.01$) and to span more than two orders of magnitude in relative pressure.

U.S. Pat. No. 4,762,010 discloses an apparatus by which gas is leaked from a bulb of known volume over the sample at a rate that is claimed to be sufficiently low to maintain equilibrium. The patent asserts that in this manner points in the adsorption isotherm can be determined continually, and that leaking gas from a controlled volume system at reduced pressures over the sample can provide better control of the amount of gas exposed to the sample. These improvements are claimed to enable the measurement of adsorption isotherms for samples with extremely large surface areas and pore dimensions down to five angstroms. The patent is based on the fact that, "Most prior work in this field has involved larger dimensions." As discussed in detail in this 1988 patent, the systems, "presently available do not satisfy the needs of the art."

This patent is based upon an improvement over U.S. Pat. No. 4,487,213 which first disclosed a leak of gas over a sample which is controlled by a mass flow controller (from a source of adsorbent gas above its saturation pressure). The patented improvement utilizes a source of gas that is filled to below the saturation pressure. In this manner the differential in pressure between the source and the sample is decreased. This is most significant for the measurement of adsorption at low equilibrium pressures (below 0.1 atmospheres) where the smaller pores are filled. By controlled increases in the pressure of the source (employing a series of reservoirs up to 5 liters in volume), a large range of pressures can be studied with reduced differences in pressure between the source of the adsorbing gas and the sample compared to a controlled flow from a source at a single pressure. In all embodiments of this invention, the adsorbing gas is admitted to the sample by flow through a flow restrictor which is claimed to keep the rate of gas admission low enough to maintain adsorption equilibrium. The volume admitted to the sample is calculated from measurement of changes in the pressure at the fixed volume source during the controlled leaking over the sample and not by measuring and controlling the flow. The patented apparatus employs two devices for pressure measurement over a range of pressures. A diffusion pump "possibly assisted by a forepump" is employed during desorption studies to as low as $10^{-5}$ Torr.

Two additional types of experiments are described in U.S. Pat. No. 4,762,010 wherein constant pressure adsorption measurements can be made by controlling the leak valve and monitoring the pressure of adsorbate over the sample, and wherein "pulses" of gas are admitted or removed by unrestricted flow between the sample and the reservoir for a prescribed period of time. Both of these methods collect non-equilibrium data, presumably to measure transient transport/diffusion, and are not relevant to the methods and apparatus of the current invention which describes improvements to measure sorption at equilibrium.

Comments on U.S. Pat. No. 4,762,010 and U.S. Pat. No. 4,487,213

U.S. Pat. No. 4,762,010 is the first to have claimed the capability to measure equilibrium adsorption isotherms over several orders (greater than a factor of 100) of magnitude of pressure. This is accomplished by employing several reservoirs of the adsorbing gas at variable pressures. However, U.S. Pat. No. 4,762,010 claims that equilibrium adsorption isotherms can be measured during the leaking of gas from the reduced pressure into the adsorption system. They point out that the flow control disclosed in U.S. Pat. No. 4,487,213 is inadequate for pressures in the 0–15 Torr range. All of the independent claims in U.S. Pat. No. 4,762,010 (claims 1, 11, 15, 16, 17, 27) employ a "flow restrictor". We find that any continuous introduction of an adsorbing gas will not be at equilibrium at the lowest pressures ($P/P_o < 0.001$). The apparatuses disclosed make no provisions or claims to achieve the lowest pressures (below $10^{-5}$ Torr) that we find are necessary during pretreatment, i.e., before the initial pressure measurements. We find that two pressure measurement devices with two full scale ranges are inadequate to accurately measure pressures from 1000 Torr to less than $10^{-5}$ Torr. The 1 Torr pressure transducer disclosed employed in U.S. Pat. No. 4,762,010 is not accurate below 0.01% of its range, i.e., below $10^{-4}$ Torr. The apparatus disclosed in U.S. Pat. No. 4,762,010 FIG. 3 is far more complex than is necessary if gas is not flowed over the sample.

U.S. Pat. No. 4,972,730 discloses an apparatus that automatically measures the saturation pressure after measurement of the adsorption isotherm. The purpose is to precisely calculate the relative pressure for subsequent calculations of morphological characteristics such as surface area and pore dimensions. This patented series of measurements and the associated apparatus are based on a claimed improvement in the determination of saturation pressure by direct measurement employing the same pressure measurement devices as those employed during the determination of the adsorption isotherm. There are no disclosures in U.S. Pat. No. 4,972,730 to enable adsorption measurements at relatively low pressures.

Improvements and Embodiments of the Current Invention

The apparatus and method of this invention represents a substantial improvement over known systems to measure equilibrium adsorption isotherms (volume adsorbed versus pressure at essentially constant temperature) accurately for pressures commencing significantly below 0.01 atmosphere and spanning several orders of magnitude in pressure (e.g., $0.01 < P/Po < 0.00001$, where Po is the saturation pressure of the adsorbent). The system employs larger tubing (>0.25 inch in outer diameter) and valves for the majority of the volume of the flow path from the sample to source of the vacuum than in conventional systems. The system uses higher capacity (lower ultimate vacuum) pumps to evacuate the sample than are found in systems currently patented for the analyses of adsorption isotherms. The invention doses increasing (and/or possibly decreasing) incremental amounts of a sorbing gas over the sample being characterized. The invention allows a variation in the amount of sorbing gas exposed to the sample during the measurement and a variation in the time between the successive additions (or removals) of sorbing gas exposed to the sample. The invention employs at least two pressure measurement devices, one of which may involve changes in its maximum range of pressure within the same unit.

These measurements are employed in the characterization of the void dimensions of microporous (dimensions less than 20 Å in diameter for an equivalent cylindrical pore) solids. These improvements enable the measurement of equilibrium adsorption isotherms over several orders of magnitude in pressure to be completed in a minimal period of time.

Measurement of Sorption Isotherms at Low Pressures

In general, the major difficulties in the measurement of adsorption isotherms at low pressures (in the order of $10^{-5}$ Torr in the case of micropores) is the addition of small amounts of adsorbate gas and the accurate measurement of the resulting equilibrium pressures. In order to overcome these difficulties we developed a modified static technique and apparatus to employ this technique.

The difference between our technique and the techniques employed by prior investigators is that the adsorbate gas is dosed over the sample through a dosing valve (or combination of vacuum valves). In this way, the amount of adsorbate gas admitted into the system is measured and is controlled. Each dose corresponds to increases in relative pressures ($P/P_o$) of less than $10^{-6}$ per dose for Ar at 87 K. or $N_2$ at 77 K. for the initial doses of gas over the sample. The system is allowed to equilibrate for a variable time before the next aliquot of adsorbate is introduced over the sample.

Helium may be first added into the system to determine the "dead volume" of the sample and sample cell from the relationship between pressure and volume added. The dead volume is the volume of the sample holder excluding that of the sample itself. After the evacuation of the helium, the adsorbate gas addition follows. Note that helium may be run into the system continuously through a flow controller for the determination of the dead volume in order to reduce the measurement time. An added advantage of the exposure to helium prior to the adsorption measurement is that the large heat transfer coefficient of helium assures rapid equilibration between the sample and the liquid nitrogen or argon temperature baths.

When the adsorbate gas is dosed into the sample cell, the pressure goes up. As adsorption takes place, the pressure decreases. The system is allowed to equilibrate before the next aliquot of adsorbate is dosed. Equilibrium is reached when the pressure no longer changes with time. The time required for equilibrium to be achieved varies from more than 30 minutes for the initial doses at residual pressures below $10^{-4}$ torr to less than 3 minutes for pressures approaching one torr ($P/Po \sim 10^{-3}$). There is no known method by which a system that employs continuous flow of gas over the sample can measure equilibrium pressures during the flow process for the measurement of adsorption at the low pressures required for the adsorption and filling of pores less than 2 nm in dimension.

The size of the dose is varied throughout the measurement of the isotherm. Initially doses in increments less than $10^{-3}$ torr ($P/Po<10^{-6}$) are added. If equal size doses were added, over a thousand doses would be required to span the pressures to $P/P_o = 10^{-3}$ in increments of $P/P_o<10^{-6}$, as required for the initial doses. If equal times were allowed for equilibrium between doses of adsorbent, one thousand increments of equilibrium time would be needed. The amount of the gas dosed is varied by up to an order of magnitude (increasing with pressure) and the time for equilibrium (decreasing with pressure) is also varied varied by up to an order of magnitude to assure accuracy in the equilibrium pressure and to minimize the total time of the measurement.

Conventional automated systems employ 10-Torr and 1000-Torr (maximum range) pressure transducers for the measurement of pressures at equilibrium. The transducer manufacturers claim accuracy down to <0.1% of their full range. So, the combination of these transducers will accurately measure pressures from 0.01 up to 1000 Torr. For adsorption of a gas at its saturation pressure this means accurate measurement in relative pressure, $P/Po$, from $10^{-5}$ to 1. So, in order to study any adsorption that may occur over ranges in relative pressures from $10^{-6}$ to $10^{-3}$, where micropores (<2 nm in diameter) fill, it is necessary to employ a more accurate capacitance manometer. We have used a 1-Torr, high accuracy capacitance transducer to obtain measurements of the pressure at equilibrium in the range of $10^{-6}<P/P_o<10^{-2}$ in our apparatus. The range of this transducer is marginal for this application and is not adequate to monitor the initial evacuation of the sample (to below $10^{-5}$ Torr). A Tylan MVG transducer may also be employed to accurately measure the pressure. This unique transducer uses dual diaphragms to measure the pressure accurately over variable ranges. Specifically, this transducer measures pressures over a range of 1 torr down to a range of 100 microns in pressure. The measurement range is selected by an electronic circuit and may be changed by the operator or by a computer program which indirectly controls the transducer. A 1000-Torr transducer was used for the measurement of pressures higher than 1 Torr.

The calculation of the volume adsorbed at a given relative pressure in a fixed volume system involves calculating the amount of adsorbent still in the gas phase. This is subtracted from the total amount added to the system at this point. The difference is the amount adsorbed. The amount of adsorbate in the gas phase, a "dead volume correction", is calculated from the product of the dead volume of the adsorption manifold (including that over the sample and accounting for the possible differences in temperature) multiplied by the measured pressure. Inaccurate calculations of the amount adsorbed are a result of inaccuracies in the dead volume, in the pressure measurements, or in the corrections for differences in temperatures of the volumes which comprise the dead volume. Prior adsorption systems developed primarily for measurements at relative pressures above 0.01 decrease the inaccuracies by minimizing the dead volume. This is accomplished by employing small volume valves and small diameter tubing to interconnect the parts of the manifold.

Adsorption in micropores occurs at substantially lower pressures than for samples which contain larger pores. Pores less than 2 nm in dimension (diameter or width) are filled at relative pressures less than 0.001. Under these conditions the dead volume correction is small because the relative pressure is small. It is less important to minimize the dead volume in order to achieve accuracy for measurements of adsorption which occurs at low relative pressures (i.e., less than 0.01).

For accurate measurements at low relative pressures, it is necessary to evacuate the sample and manifold to even lower pressures than the pressure of the initial measurement. Smaller tubing and valves in the system make the evacuation more difficult to achieve and require longer times to achieve these low pressures. Further, smaller tubing and valves mean that there is an increased possibility that there are differences in the pressure at different volumes of the system being evacuated; thus, pressure measurements are less accurate.

The present system avoids the dominance of small diameter tubing and small valves between the vacuum pump and the sample employed in prior adsorption systems. The majority of the tubing and valves which connect the vacuum system and the sample are larger than 0.25 inch in inner diameter, ID. Preferably this tubing is 0.5 inch ID or larger. The only tubing that most directly connects the sample and the high vacuum pump that is less than 0.5 inches OD is that volume which connects the sample to the adsorption manifold. This is because the tubing which connects immediately to the sample is less than 0.5 inch ID in order to reduce any inaccuracies which would occur if there were any variation in the height of a thermal bath in which the sample is immersed.

To achieve the low initial pressures required for the measurement of adsorption in small pores, it is necessary to employ an efficient pumping system capable of achieving a high vacuum (low pressure) over the sample. This should be at least an order of magnitude (and preferably at least two orders of magnitude) lower in pressure than the initial pressure at which adsorption may occur. Adsorption occurs below a relative pressure of $10^{-7}$ to $10^{-6}$ for adsorption in pores of a diameter less than 0.4 nm. Preferably, the pumping system should be able to efficiently evacuate the manifold and sample to less than a relative pressure of $10^{-9}$. The vacuum systems employed for most of the current automated adsorption systems employ oil diffusion pumps with a rough, backing pump. This is not adequate to reach these required vacuums efficiently. A turbomolecular pump is employed in the system being patented. Other vacuum systems could also fulfill these requirements.

Summary of Principles For the Efficient, Accurate Measurement of Adsorption At Low Relative Pressures On Which This Invention Is Based a) The pressure of adsorption is measured by more than one pressure transducer and/or employing transducers that have more than a single maximum range. The range of the pressure measuring device is such that pressures of 0.001 torr (and preferably 0.0001 torr, i.e., ca. $10^{-7}$ atm.) are measured accurately.

b) Gas is dosed over the sample and the volume of the gas dosed between measurements is changed as the measurement pressure changes.

c) The time between doses varies as the time required to achieve equilibrium.

d) The tubing connecting the pumping system and the sample and the sample and the pressure transducers is of diameter greater than 0.25 inch in inner diameter ID (and preferably equal to or greater than 0.5 inches OD), however, the tubing immediately connected to the sample may be of OD equal to or less than 0.25 inch. The volume of this smaller diameter tubing should be less than 10% of the total volume of the closed system into which the adsorbing gas is dosed.

e) The pumping system employed to evacuate the closed system into which the adsorbing gas is dosed should be capable of reaching pressures less than $10^{-8}$ atmospheres in this system (and preferably less than $10^{-9}$ atmospheres pressure).

DESCRIPTION OF AN IMPROVED SYSTEM TO CONDUCT ADSORPTION AT LOW RELATIVE PRESSURES

Figure 1:
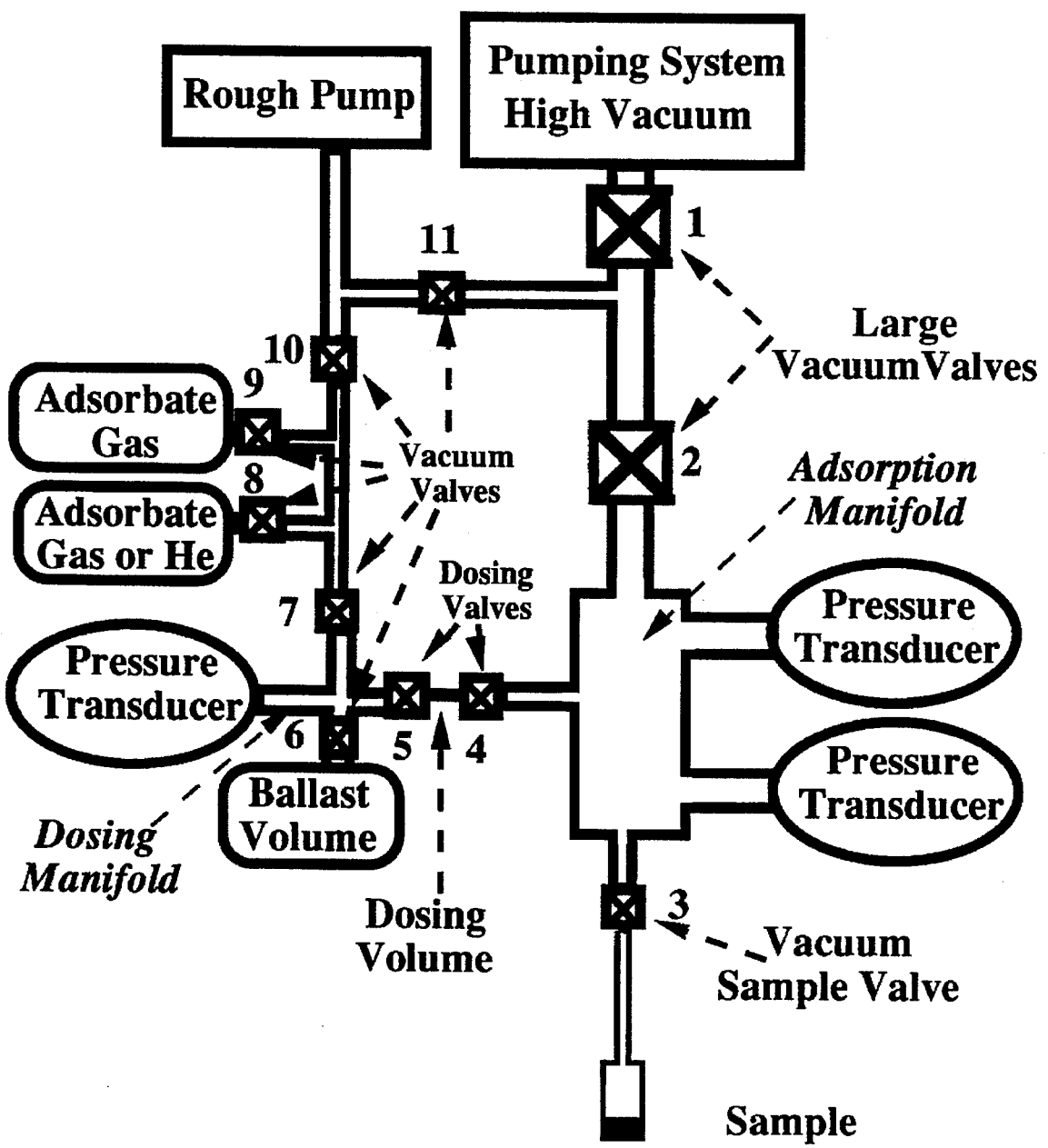
FIG. 1 is a schematic drawing of an illustrative apparatus capable of measuring sorption isotherms in accordance with this invention.

FIG. 1 is a schematic diagram of an adsorption system which represents a preferred embodiment of this invention and can be operated to perform the method of this invention. Modified configurations apparent to those skilled in the art could could be employed to practice the invention and to achieve equivalent advantages.

The system contains two pumping systems: a high vacuum turbomolecular pump and backing pump; and a separate rough pump. The high vacuum pump is connected to a manifold (volume connected to several valves and transducers) by two high vacuum valves 1 and 2. These valves contain orifices greater than 0.25 inch in diameter as does all the tubing that connects the high vacuum pumping system and this "adsorption manifold" directly. The adsorption manifold comprises the volume contained between valves 2, 3 and 4. The manifold is connected to two pressure transducers which span different ranges, for example, 0–1000 Torr and 0–1 Torr. This lower range transducer may also be of the variable range multiple-diaphragm type such as the TYLAN® model MVA which has a most sensitive range of 0–100 microns of mercury. The manifold is also connected to the sample by a vacuum valve 3. This is the only portion of the system in direct line between the pumping system and the sample which may be (approximately) equal to or less than 0.25 inch ID. The sample may be immersed in a liquid (such as liquid nitrogen or other thermal bath) in order to maintain the temperature of the sample at a near constant temperature which may differ from that of the manifold. The manifold is also connected to a dosing system by a vacuum valve 4.

A dosing volume is contained between vacuum valves 4 and 5; however, a single dosing valve of the type commonly employed in gas or liquid chromatography to introduce a small amount of sample into the carrier fluid may also be employed. The term "dosing" means that a fixed volume is employed to introduce or to remove gas from the adsorption manifold. This procedure differs from "pulsing" wherein a single valve may be opened for a period of time to admit an amount of gas from one part of the system into the adsorption manifold.

A second manifold, the dosing manifold, for filling the dosing volume consists of the volume between vacuum valves 5 and 7. It is connected to a pressure transducer, for example having a range of 0–1000 Torr. It is also connected through vacuum valve 6 to a ballast volume which is connected to or isolated from the dosing manifold by opening or closing valve 6. A third manifold, the inlet manifold, between vacuum valves 7 and 10 is connected to the adsorbing gas (or a non adsorbing gas such as He) by vacuum valves 8 and 9. This inlet manifold may also be evacuated by the rough pump (via valve 10) or the high vacuum pump (via valve 11) in this configuration.

Operation of the Improved System to Conduct Adsorption At Low Relative Pressures The adsorption measurements can be achieved by the following sequence of operations:

1) The sample and adsorption manifold are evacuated to low pressures, e.g., less than $10^{-8}$ atmospheres. This is accomplished with valves 1, 2, and 3 open and valves 4 and 11 closed. The pressure transducers on the adsorption manifold may be used to monitor the pressure while a separate pressure measuring device may be employed to monitor the ultimate pressure. The pressure transducers can be zeroed at this low pressure as needed.

2) The adsorption manifold and sample are isolated by closing valve 3.

3) Gas is admitted to the inlet manifold (which has also been evacuated by the rough pump or by the high vacuum pump prior to step 1). Valve 8 or valve 9 is opened with valves 10 and 7 closed.

4) The gas is then admitted to the dosing manifold (which had been evacuated previously) by manipulation of valves 7 and 6. Opening valve 6 decreases the pressure in the dosing manifold as the gas within it expands to fill the ballast volume. If the dosing manifold pressure is to be low, valve 7 is opened while valve 6 is closed then valve 7 is closed and valve 6 is opened. The pressure is monitored by the pressure transducer connected directly to the dosing manifold. The alternate opening and closing of valves 6 and 7 can be repeated until the desired dosing pressure is reached. If a larger amount of gas (i.e., a higher dosing pressure) is desired in the dosing manifold, then valve 7 can be opened (and then closed) with valve 6 open.

5) The dosing volume is filled with the gas by opening valve 5 while valve 4 remains closed, and the pressure is monitored by the pressure transducer attached to the dosing manifold. Then valve 5 is closed.

6) The gas is dosed into the adsorption manifold (and over the sample) by opening valve 4. The pressure is monitored with one (or both) of the pressure transducers directly attached to the adsorption manifold.

Subsequent Doses

After equilibrium is achieved (see below), subsequent doses of gas may be admitted to the sample by repeating steps 5) and 6) if similar doses of adsorbing gas are desired. This is because the Ballast volume is much larger than the dosing volume. In all cases, the actual pressure in the dosing volume admitted to the sample and adsorption volume is measured by the pressure transducer attached to the dosing manifold. If increased dose sizes are desired, steps 3) and 4) can be repeated to increase the pressure in the dosing manifold. Subsequently, steps 5) and 6) are performed to admit the dose over the sample.

Allowing Differences In Time of Attainment of Equilibrium and Therefore the Time Between Doses of Gas Over the Sample The pressure in the adsorption manifold and over the sample is monitored until equilibrium is achieved. At the same time, the temperatures of the manifold and of the sample are monitored. Equilibration may take considerable time (up to the order of 100 minutes) or may take much shorter times. Equilibrium is determined from a measured lack of change in the pressure with time (i.e., less than a predetermined limit in the changes in pressure with time). This attainment of equilibrium can be monitored automatically with a controller or a computer, or by an operator who monitors the pressure and can manually override the automatic system. In general, more time is required to attain equilibrium in adsorption and in temperature at lower pressures.

Changes In the Amount of Gas Dosed Over the Sample

As noted above in "Subsequent doses", the amount of gas dosed over the catalyst can be changed from one dose to another. The size of the dose will be increased by increasing the pressure in the dosing manifold which is used to fill the dosing volume. Also, the amount dosed over the sample can be increased by admitting multiple doses of similar size between periods when the pressure is monitored to determine the attainment of equilibrium. The amount of gas admitted between measurements of equilibrium pressures for a given amount of gas admitted is determined by the operator or is automatically controlled by a computer. A variety of algorithms may be employed to change the size of the doses as the pressure is increased during adsorption or decreased during desorption. This invention allows the operator to determine the optimum procedure for controlling the amount of gas admitted to or removed from the adsorption manifold and over the sample.

The Use of a Controlled Leak of Adsorbing Gas Into (or out of) the Adsorption Manifold It is necessary to dose the adsorbing gas into the adsorption manifold to achieve equilibrium at low pressures (e.g., less than $10^{-4}$ atmospheres). If pressure is increased, equilibrium may be achieved while adsorbing gas is leaked into the adsorption manifold and over the sample. The apparatus described above could be modified to incorporate a flow control valve between the dosing or inlet manifolds, and the adsorption manifold. Alternatively, one of the valves (e.g., valves 7, 8, or 9) could be replaced with a flow control valve or a flow control valve could be present in parallel with these valves. In this manner, this apparatus could be modified such that it may be operated in a manner that allows for doses of adsorbate to be introduced to the sample over a desired range of pressure and the adsorbate can be introduced over the sample by a controlled flow over another range of pressures. The embodiments of this invention do not preclude flowing of gas from its source over the sample for a range of pressures. None of the prior patents claim and none of the systems employed for the measurement of adsorption isotherms employ a combination of adsorbent dosing at low pressures and adsorbent flow at higher pressures. This unique combination of approaches has distinct advantages over known technology in this area.

Measurement of Desorption

This system can also be operated to measure the desorption isotherm, which is the equilibrium amount adsorbed at a given pressure when the pressure is being decreased at a constant temperature. This is accomplished by modifying the sequence of steps outlined above in the following manner.

1) The sample manifold and sample are allowed to achieve equilibrium with a known amount of gas at a desired initial pressure. This may be done by performing the sequence of steps outlined above for measurement of the adsorption isotherm.

2) The inlet manifold is evacuated via valve 10 and/or valve 11 with valves 7, 8 and 9 closed. Then valves 10 and 11 are closed.

3) Gas is then removed from the dosing manifold by manipulation of valves 7 and 6. If the dosing manifold pressure is to be lowered a small amount, valve 7 is opened while valve 6 is closed then valve 7 is closed and valve 6 is opened. The pressure is monitored by the pressure transducer connected directly to the dosing manifold. These steps can be repeated until the desired pressure in the dosing manifold is reached. If a larger amount of gas is to be removed, then valve 7 can be opened (and then closed) with valve 6 open.

4) The dosing volume is evacuated by opening valve 5 and the pressure is monitored by the pressure transducer attached to the dosing manifold. Then valve 5 is closed.

5) The gas is removed from the adsorption manifold (and over the sample) by opening valve 4. The pressure is monitored with one (or both) of the pressure transducers directly attached to the adsorption manifold.

If a larger amount of gas is to be removed then the volume connecting valves 4, 7, and 6 can be evacuated by opening valves 10, 7 and 5 with valves 4, 6, 8 and 9 closed and then valve 7 is closed. Subsequently, valve 4 is opened which allows the gas in the adsorption manifold to expand into the volume up to valves 6 and 7. An even larger volume of gas can be removed from the adsorption manifold (and over the sample) by allowing the gas to expand into the ballast volume as well (by keeping valve 6 open during evacuation and the opening of valve 4). In these ways (and by other manipulations of the valves) the volume of gas removed from the system can be varied as desired during desorption.

Calculations of the Amount Sorbed

The amount sorbed (adsorbed or desorbed) at a given pressure is calculated by a method similar to the methods employed in all static adsorption apparatus and is not unique to this invention. In general, the amount of total gas present in the adsorption manifold (and over the sample) is calculated from the measured amounts of gas admitted to the system during adsorption or from calculating the amount admitted and subtracting the amount removed during desorption. The amount of gas still present in the gas phase within the adsorption manifold and over the sample is calculated from the measured equilibrium adsorption pressure and the measured "dead volume" of the sample and adsorption manifold. The difference between the amount present in the adsorption manifold (and over the sample) and the amount present in the gas phase is the amount adsorbed on the sample.

Measurement and Calculation of the "Dead Volume" of the System

The dead volume is the volume contained in the adsorption manifold and over the sample excluding the volume of the sample. It is therefore the volume that would be occupied by a gas that does not adsorb on the sample. It is often converted to an equivalent volume assuming the adsorption manifold and the volume over and surrounding the sample were at the same temperature. Thus, it is common to perform the calculations of the amount of gas still in the gas phase as if it were contained in an equivalent total volume at the temperature of the manifold.

As the dead volume can vary depending on the sample holder volume and the actual volume of the sample, the dead volume is actually measured by performing steps similar to those employed in the adsorption measurements with a non-adsorbing gas such as He at temperatures above the critical point of He (~5 K.) or by flowing He at a fixed rate into the adsorption manifold and measuring the change in pressure with time. The equivalent volume (at one atmosphere and the manifold temperature) is calculated by dividing the change in pressure with time into the volumetric flow rate if flow is employed or by dividing the average pressure increase for each dose into the dose volume (corrected for the dose pressure and temperature) if dosing is employed.

An Example of a Measured Isotherm

Figure 2:
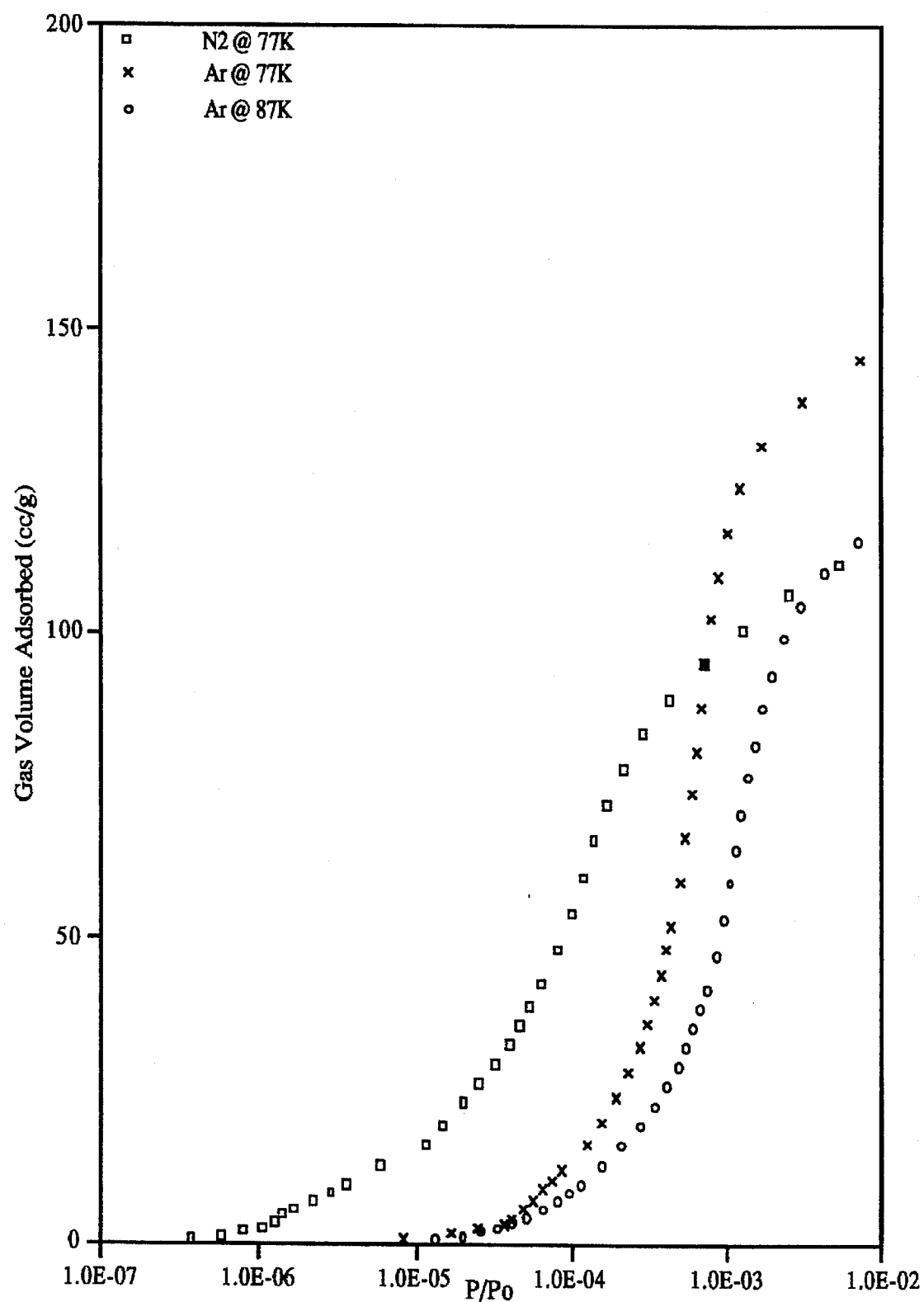
FIG. 2 is a graph of Zeolite Y adsorption isotherms for $N_2$ at 77 K., and Ar at 77 and 87 K., as measured by the apparatus and methods of this invention.

Typical adsorption isotherms for the adsorption of nitrogen at –77' K. and Argon at 77 K. and 87 K. onto a sample of Y-zeolite as measured by the procedures described in this invention are shown in FIG. 2. Each point on the graphs represents a single equilibrium adsorption measurement. It is readily seen that the differences between the pressures where the measurements are made is increased over the sequence of measurements, i.e., increments of relative pressure (P/Po) less than $1\times10^{-6}$ are employed for the lowest pressures and increments of relative pressure (P/Po) greater than $1\times10^{-5}$ are employed for the higher pressures. The increments in pressure increased by over one order of magnitude because the amount of gas dosed over the sample was increased by over an order of magnitude. Further, the time required to achieve adsorption equilibrium between doses was found to range from greater than 30 minutes for the doses at lower pressures to less than 3 minutes for the higher pressures. Thus, the time between doses was varied by more than order of magnitude over the course of the measurements. The improved apparatus described in this invention is able to perform these measurements with variations in the amount of gas admitted to the sample and variations in the time between measurements by the procedures described above. This flexibility in operating procedures (changes in the size of the doses and the time between doses) represents a significant improvement over previously known systems.

It will be understood that the exemplary system described above includes means for controlling and measuring of the temperature at which the sample is maintained, for example by immersing the sample and a portion of the tubing connecting the sample and the adsorption manifold in a bath maintained at the desired temperature or by other well known means.

While a preferred embodiment of this invention has been described, it will be appreciated by those skilled in the art that numerous modifications and improvements thereon can be made without departing from the spirit and scope of the invention. Thus, for example, desorption may also be conducted by a variety of procedures as outlined above in Measurement of Desorption (e.g., step 5). Therefore the present invention is not to be measured by the above exemplary disclosure but only by the following claims.

What is claimed is:

1. Apparatus for measuring the equilibrium amount of sorption of a sample which comprises:

a dosing manifold whose volume is accurately measured and is fixed, means for accurately monitoring the pressure within said dosing manifold, an adsorption manifold whose volume is accurately measured and fixed connected to the contained sample, means for measuring the pressure of gas in the adsorption manifold capable of accurately measuring pressures of 0.001 mm Hg, means for dosing volumetric increments of gas from the dosing manifold into the adsorption manifold, and a primary vacuum system directly connected to the adsorption manifold by tubing at least 0.25 inches in ID and capable of reaching pressures less than $10^{-6}$ mm Hg in the adsorption manifold.

2. The apparatus of claim 1 wherein the dosing manifold is connected through a vacuum valve to a ballast volume whose volume is larger than that of the rest of the dosing manifold.

3. The apparatus of claim 1 wherein the connection between the sample manifold and the primary vacuum system is accomplished with valves whose orifice is greater than 0.25 inches.

4. The apparatus of claim 3 wherein the volume dosed between the dosing manifold and the adsorption manifold comprises the volume in the tubing connecting two on/off vacuum valves.

5. The apparatus of claim 1 wherein the means for dosing between the dosing manifold and the adsorption manifold comprises a vacuum valve.

6. The apparatus of claim 1 further including means for changing the amount of gas in the dosing manifold by which means the absolute pressure can be changed by at least an order of magnitude.

7. The apparatus of claim 6 wherein at least two pressure measuring devices are employed to measure the pressure in the adsorption manifold and the pressure range of one of these transducers is less than 1 torr.

8. The apparatus of claim 6 wherein the means for measuring the pressure in the adsorption manifold comprises at least one transducer which is capable of measuring pressures over several ranges of total pressure.

9. The apparatus of claim 6 wherein the means for measuring the pressure in the adsorption manifold comprises a multiple diaphragm pressure transducer.

10. The apparatus of claim 9 where the multiple diaphragm pressure transducer employed is a TYLAN® model HVG.

11. The apparatus of claim 6 which further includes computer means whose input is connected to the means for measuring pressure in the dosing manifold and the adsorption manifold.

12. The apparatus of claim 11 which further includes a computer which controls the operations of the apparatus, which may be the same as employed for the purpose described in claim 11.

13. The apparatus of claim 6 which also includes a flow control valve to introduce gas into the adsorption manifold.

14. Apparatus for measuring the equilibrium amount of sorption of a sample which comprises:

a source of adsorbate gas maintained at a constant pressure, means for accurately measuring or controlling the source pressure, an adsorption manifold whose volume is accurately measured and fixed connected to the contained sample, means for measuring the pressure of gas in the adsorption manifold capable of accurately measuring pressures of 0.001 mm Hg, means for dosing volumetric increments of gas from the source of adsorbate gas into the adsorption manifold, and a primary vacuum system directly connected to the adsorption manifold by tubing at least 0.25 inches in ID and capable of reaching pressures less than $10^{-6}$ mm Hg in the adsorption manifold.

15. The apparatus of claim 14 wherein the connection between the adsorption manifold and the primary vacuum system is accomplished with valves whose orifices are greater than 0.25 inches.

16. The apparatus of claim 14 wherein the dosing manifold is connected through a dosing valve to a ballast volume whose volume is larger than that of the rest of the dosing manifold.

17. The apparatus of claim 16 wherein the volume dosed between the dosing manifold and the adsorption manifold comprises the volume in the tubing connecting two on/off vacuum valves.

18. The apparatus of claim 14 wherein the means for dosing volumetric increments of gas between the dosing manifold and the adsorption manifold comprises a vacuum valve.

19. The apparatus of claim 14 wherein the means for measuring the pressure in the adsorption manifold comprises at least two transducers at least one of which transducers has a pressure range of less than 1 torr.

20. The apparatus of claim 19 wherein at least one of said transducers is a multiple diaphragm pressure transducer.

21. The apparatus of claim 20 wherein the multiple diaphragm pressure transducer employed is a TYLAN® model HVG.

22. The apparatus of claim 19 which further includes computer means whose input is connected to said transducers.

23. The apparatus of claim 22 wherein said computer means controls the operations of the means for dosing volumetric increments of gas from the dosing manifold into the adsorption manifold.

24. The apparatus of claim 16 which also includes a flow control valve to introduce an adsorbent or a non adsorbing gas into the adsorption manifold.

25. A method for measuring adsorption by a sample, comprising the following steps:

disposing the sample in an adsorption chamber, evacuating said sample and the adsorption chamber to a pressure less than $10^{-6}$ mm Hg, dosing into the adsorption chamber an initial dose of adsorbent of such volume that the pressure (P) of gas in the adsorption chamber is raised to a level less than 0.001 in relative pressure (P/Po, where Po is the saturation pressure of the adsorbent) before adsorption occurs, dosing into the adsorption chamber subsequent doses of adsorbent whose volumes are changed as the equilibrium adsorption pressure changes, measuring the pressure and temperature in the adsorption chamber following each such dose or set of doses, and determining the amount of gas adsorbed by the sample as a function of the equilibrium pressures.

26. The method of claim 25, wherein the amount of adsorbent added to the adsorption chamber between measurements is changed by at least an order of magnitude over the course of a series of adsorption measurements.

27. The method of claim 26, wherein the amount added into the adsorption chamber is dosed from a fixed volume manifold whose pressure is changed by over an order of magnitude.

28. The method of claim 26, wherein more than one dose of adsorbent is added to the adsorption chamber between measurements.

29. The method of claim 26, wherein the time between additions of gas is varied by up to an order of magnitude over the course of a series of adsorption measurements to allow for equilibrium to be achieved between measurements.

30. The method of claim 29, wherein a computer controls the amount of gas admitted to the sample and the time between measurements.

31. The method of claim 25, wherein a flow control valve is employed to add gas into the adsorption chamber for pressures of the adsorbate in the sample manifold above a desired pressure.

* * * * *